United States Patent [19]

Nyström et al.

[11] Patent Number: 6,113,875
[45] Date of Patent: Sep. 5, 2000

[54] **DIAGNOSTIC PREPARATION FOR DETECTION OF *HELICOBACTER PYLORI***

[75] Inventors: Christer Nyström; Thomas Lundqvist, both of Uppsala; Anders Pettersson, Kode, all of Sweden

[73] Assignee: Diabact AB, Uppsala, Sweden

[21] Appl. No.: 08/836,282

[22] PCT Filed: Oct. 17, 1995

[86] PCT No.: PCT/SE95/01212

§ 371 Date: May 29, 1997

§ 102(e) Date: May 29, 1997

[87] PCT Pub. No.: WO96/14091

PCT Pub. Date: May 17, 1996

[30] Foreign Application Priority Data

Nov. 2, 1994 [SE] Sweden ................................. 9403755

[51] Int. Cl.$^7$ ........................... A61K 51/00; A61K 49/00
[52] U.S. Cl. ...................... 424/1.29; 424/1.33; 424/1.25; 424/1.81; 424/9.1
[58] Field of Search ..................... 424/1.33, 1.29, 424/1.25, 1.11, 1.81, 451, 489, 9.1; 600/300, 532; 436/811; 435/12; 514/588

[56] References Cited

U.S. PATENT DOCUMENTS

| | | | |
|---|---|---|---|
| 4,830,010 | 5/1989 | Marshall | 600/300 |
| 4,923,801 | 5/1990 | Marshall et al. | 435/12 |
| 5,064,650 | 11/1991 | Lew | 424/435 |
| 5,542,419 | 8/1996 | Moulton-Barrett et al. | 128/630 |

FOREIGN PATENT DOCUMENTS

| | | |
|---|---|---|
| 294 634 | 10/1991 | Germany. |
| 61-191610 | 8/1986 | Japan. |
| 62-503033 | 12/1987 | Japan. |
| 1-501934 | 7/1989 | Japan. |
| 2-3606 | 1/1990 | Japan. |
| 5-246861 | 9/1993 | Japan. |
| WO86/06625 | 11/1986 | WIPO. |
| WO87/05804 | 10/1987 | WIPO. |
| WO 95/11672 | 5/1995 | WIPO. |

OTHER PUBLICATIONS

Lachman et al., The Theory and Practice of Industrial Pharmacy, 1976, pp. 329–331, Lea & Febiger, Philadephia.
Lieberman et al., *Pharmaceutical Dosage Forms*, vol. 1, 1980, pp. 3–4, Marcel Dekker, Inc., New York.
Marshall et al., "A 20–Minute Breath Test for *Helicobacter pylori*", The Americal Journal of Gastroenterology, vol. 86, No. 4, 1991, pp. 438–445.
Lotterer et al., "The simplified $^{13}$C–urea breath test—One point analysis for detection of *Helicobacter pylori* infection", Z Gastroenterol, 1991; vol. 29; pp. 590–594.
"Tablets", *Medical Encyclopedia*, Dec. 10, 1982, p. 82, center col.
"'Application of AC–Di–Sol' to tablets", *Avisel Review*, Sep. 1, 1986, (Report No. 1) pp. 9–15; (Report No. 2) pp. 16–18.
"Cross Carmelose Sodium", *Dictionary of Medical Adjuvants*, Jan. 14, 1994; p. 46.
"Unit Operation and Machines for Formulations", *Development of Medicines*, vol. 11, Nov. 10, 1989, pp. 2–5.
E. Lotterer et al., "The 13C—urea breath test—detection of *Helicobacter pylori* infection in patients with partial gastrectomy", Dialog Information Services, Feb. 1993.

Primary Examiner—Jose' G. Dees
Assistant Examiner—Michael G. Hartley
Attorney, Agent, or Firm—Young & Thompson

[57] ABSTRACT

A preparation for administering isotope-labelled urea together with acid in a solid form that is influenced by activity of *Helicobacter pylori* in the stomach only, avoiding any non-Helicobacter (unspecific) urease activity in the oral cavity and the pharynx. The preparation dissolves very quickly in the stomach. The preparation is used to show increased urease activity in the stomach in association with an ongoing *Helicobacter pylori* infection.

8 Claims, No Drawings

DIAGNOSTIC PREPARATION FOR DETECTION OF *HELICOBACTER PYLORI*

This application is a 371 of PCT/SE95/01212, filed Oct. 17, 1995.

Diseases relating to gastric ulcers, are a serious public health problem and cost the community large sums of money in the form of medical costs and lost working ability. It has been fully established that the presence of *Helicobacter pylori* in the stomach is a necessary prerequisite for the development of stomach ulcers and/or duodenal ulcers. If the bacterium is not present in the stomach, no ulcer will develop. It has also been established that when a *Helicobacter pylori* infection is cured with the aid of antibiotics, there will be no relapse in stomach ulcer diseases. Stomach ulcer diseases are therefore considered to be bacterium-caused diseases which can and shall be cured.

There is a great need for a reliable and simple diagnosis in this regard, as large patient populations inflicted with gastrointestinal problems will need to be examined with regard to the presence of a *Helicobacter pylori* infection.

The present invention is based on the observation that the bacterium *Helicobacter pylori* produces the enzyme urease in very large quantities. The enzyme urease is normally not found in human beings, and its presence in the stomach indicates that *Helicobacter pylori* is present. *Helicobacter pylori* has established an ecological niche in the human stomach. The bacterium thrives in a neutral pH, which is found beneath the mucus layer in the stomach. The bacterium produces large quantities of the enzyme urease, which in turn catalyzes the degradation of urea to ammonia and bicarbonate. The bicarbonate is then converted in the acid environment of the stomach to carbon dioxide and water.

In Sweden, about 470,000 patients seek medical care for stomach ulcer-like problems each year. The possibility of being able to diagnose and to treat *Helicobacter pylori* infections in a reliable and simple manner is therefore of great interest to the patient and also from the aspect of health economy.

The present invention pertains to a solid preparation for simple and reliable diagnosis of ongoing urease activity in the stomach in conjunction with *Helicobacter pylori* infection.

Present-Day Methods of Showing the Presence of *Helicobacter pylori*

Biopsy Methods

A common feature of these methods (cultivation of the bacterium, histological examination, quick urease test) is that they are carried out on biopsy material. This means that the patient must undergo a gastroscopic examination of the stomach with the use of fibre optics, during which tissue samples are taken from the stomach epithelium. This examination is both expensive and unpleasant to the patient.

Serological Methods

A common feature of these methods consists of determining the presence of specific antibodies against *Helicobacter pylori* in the blood or in stomach secretion. One drawback with these methods is that it is necessary to take blood samples or secretion from the stomach. Neither are serological methods able to show the presence of bacteria on the occasion of making the examination.

It takes about twenty days from the time of being infected with *Helicobacter pylori* to the time that antibodies against the bacterium manifest themselves.

After successful treatment of the bacterial infection, elevated contents of antibodies remain in the blood for a very long time, thereby greatly limiting the possibility of accurately checking the condition of treated patients.

Urea-Breath Tests

The method is based on the production of the enzyme urease by the bacterium *Helicobacter pylori*. Urease catalyzes the degradation of urea to ammonia and bicarbonate. The bicarbonate is then converted to carbon dioxide and water in the acid environment of the stomach.

At present, the urea-breath test is performed in the following manner: The patient swallows an aqueous solution containing isotope-labelled ($^{11}C$, $^{13}C$, $^{14}C$) urea. In the presence of urease-producing *Helicobacter pylori* and acid in the stomach, urea is broken down so that the isotope-labelled carbon atoms convert to carbon dioxide and are secreted via the exhaled air. The amount of isotope-labelled carbon dioxide in the exhaled air is determined.

The advantages of this method are that the examination is non-invasive, i.e. the patient need not be subjected to instrumentation (gastroscopy) and neither need blood samples be taken or samples of secretion taken from the stomach. Furthermore, because the urea supplied to the patient disperses over the whole surface of the stomach, the fact that the bacterium has a very spotty distribution area lacks significance.

The urea-breath test is disadvantageous on three separate counts:

1. Isotope-labelled urea is ingested as an aqueous solution. This means that the urea can be broken down by urease-producing bacteria in the oral cavity and the pharynx of the patient, which may result in falsely positive indications regarding the presence of *Helicobacter pylori*.

2. In order for the test to be successful, it is necessary for a given quantity of hydrogen ions to be present in the stomach in order for the bicarbonate formed to be converted into carbon dioxide. Many patients who suffer from stomach ulcers are treated with an acid-suppression inhibitors which gives a falsely negative test result when such patients are diagnosed in accordance with present methodology.

3. Isotope-labelled urea has only a short chemical durability in aqueous solution, which causes practical difficulties when the patient is tested clinically.

It will be evident from the foregoing that several diagnostic methods of showing the presence of *Helicobacter pylori* in the stomach are known to the art, but that these methods are encumbered with a number of disadvantages, for instance are deficient in positively showing the presence of bacteria or are unpleasant for the patient.

There is thus a need to improve such diagnostic methods so that a more reliable diagnosis can be made under all conditions, and to enhance the practical use of such methods.

General Disclosure of the Invention

By constructing a capsule, tablet or some other solid preparation that has a high rate of disintegration and contains isotope-labelled ($^{11}C$, $^{13}C$, $^{14}C$) urea in combination with an acid, the following four important advantages are obtained with urea-breath tests relating to the diagnosis of gastric ulcer diseases:

1. When isotope-labelled urea is administered in the form of a solid preparation, the degradation by urease-producing bacteria in the oral cavity and the pharynx before the urea has reached the stomach is prevented. This reduces the number of falsely positive results and therewith significantly increases the reliability of the examination.

2. The administration of a weak acid at the same time as the isotope-labelled urea is administered also enables the urea-breath test to be performed during ongoing acid-suppression inhibiting treatment. This is a significant gain, since the majority of the patients who are subjected to the urea-breath test are chronically treated with potent acid-secretion inhibiting drugs. This substantially reduces the occurrence of falsely negative results.

3. Because isotope-labelled urea and a weak acid in capsule, tablet or other solid form, are stable over a relatively long period of time, the problems caused by the limited chemical stability of urea in aqueous solution are avoided.

This affords significant practical advantages with regard to distribution and application of the urea-breath test.

4. The use of a ready-prepared solid preparation (e.g. a tablet) also affords advantages with regard to dosage accuracy and time saving, in comparison with preparing the established water-based test liquid.

In order to be able to achieve these significant advantages, it is necessary to construct the solid preparation such that it affords protection of its contents from the influence of urease in the oral cavity and in the pharynx, and also such that it will break down rapidly and completely in the stomach.

Technical Description of the Invention

There is provided in accordance with the invention an essentially water-free preparation which contains primarily either $^{11}C$, $^{13}C$ or $^{14}C$ labelled urea and an acid, for instance ascorbic acid, citric acid, tartaric acid or aciglumin, in a solid preparation intended for peroral administration to human beings. However, it should be noted that the invention is not restricted solely to urea and that the present invention also includes other substances or substrates that are influenced by the activity of *Helicobacter pylori* and that can be readily analyzed.

The preparation shall contain sufficient acid to produce a sufficiently low pH-value in the stomach when ingested. In this regard, a suitable pH value is beneath pH=4. The amount of a specific acid required to obtain a desired pH in the stomach of a patient can be determined easily by the skilled person on the basis of simple routine tests.

The pharmaceutical preparation according to the invention is composed such that isotope-labelled urea and acid will be released essentially immediately when the preparation reaches the stomach. A preferred form of the preparation includes $^{13}C$ urea and water-free citric acid. The preparation may either be a conventional tablet, optionally provided with a quickly soluble coating, although it may alternatively have the form of a capsule preparation. In this latter case, so-called hard gelatin capsules (operculate capsules) are intended, although soft gelatin capsules may also be used. The sole prerequisite is that the chemical stability is sufficiently high and that the active substance content of the preparation can be quickly released and dissolved. The chemical stability is normally improved when the active substances and auxiliary substances are present in solid form. The chemical stability will normally be sufficiently high when an oil solution is used in combination with a soft gelatin capsule.

Other solid preparations may also be used. Without limiting the list of those preparations that can be used in this regard, it can be mentioned that such preparations may include solid solutions, solid dispersions and so-called pellet preparations. By pellet preparations is meant larger or smaller grains produced by granulation or by extrusion/spheronization. The active substance can then be incorporated in these pellets or attached to their surfaces. The active pellets can then be compressed to a quickly disintegrating tablet form, or can be filled in hard gelatin capsules.

Tablets, which are the preferred form, can be produced with the aid of auxiliary substances and process steps well known to the skilled person. Thus. in order to obtain maximum rapid release and dissolution there are preferably used essentially water-soluble components and auxiliary substances which accelerate disintegration of the tablet. The auxiliary substances used may have the form of pharmaceutical bursting or disintegrating agents of a kind known to the skilled person. Particularly suitable agents in this regard are those which swell markedly in water by hydration, to a volume that corresponds to 10–20 times their dry volume. Examples of such agents include cellulose derivatives and starch derivatives in the form of cross-linked polymers which are insoluble in water but which swell markedly therein. Derivatives of polyvinyl pyrrolidone is another example of such agents. A modified cellulose-gum of high water swellability and marketed under the trade name Ac-Di-Sol® by FMC Corporation, U.S.A., is a specific example of a suitable pharmaceutical disintegrating agent. Other types of pharmaceutical disintegrating agents may also be used, and the skilled person will have no problem in choosing a suitable agent.

In the case of a particularly preferred form, the active substance urea has a very fine particulate quality. In this form, the particle size is preferably smaller than 200 μm, and more preferably smaller than 20 μm. However, this does not exclude the use of particulate active substances of larger particle size, when the remainder of the formulation so permits. Such assessments are well known to the skilled person.

EXAMPLE

Tablets were prepared in accordance with the following for the purpose of testing the invention and comparing the invention with conventional techniques (aqueous solution):

The ingredients of the following composition were mixed in a conventional double-cone rotary mixer. Tablets were then compacted in a so-called excenter press machine having 12 mm concave-faced punches.

| Composition of 1 tablet | |
| --- | --- |
| 1. Urea, $^{13}C$ | 50 mg |
| 2. Citric acid, anhydrous | 63 mg |
| 3. Avicel ® Ph 101 | 60 mg |
| 4. Ac-Di-Sol ® | 24 mg |
| 5. Magnesium stearate | 3 mg |

Avicel® Ph 101 is the trade name of a microcrystalline cellulose marketed by FMC Corporation, U.S.A.

Ac-Di-Sol® is the trade name of a modified cellulose gum of high swellability in water from FMC Corporation, U.S.A. In this case, it functions as a pharmaceutical disintegarating agent for a quick disintegration of the tablet.

In tests carried out on patients, either two tablets (corresponding to 100 mg urea) or 2.5 ml aqueous solution which also contained 100 mg urea were ingested by respective patients.

When making a comparison between isotope-labelled urea administered in accordance with a conventional technique (aqueous solution) and a preparation in accordance with the invention, isotope-labelled carbon dioxide was observed in the exhalation air of eight patients who lacked the bacterium in the stomach, after ten minutes from the time of ingesting the aqueous solution.

When isotope-labelled urea was ingested in the form of a preparation according to the invention, no isotope-labelled carbon dioxide was observed in the exhalation air of these patients.

When making a comparison between isotope-labelled urea in aqueous solution and isotope-labelled urea in solid preparation in accordance with the invention with ten patients known to have stomach bacteria, markedly elevated quantities of isotope-labelled carbon dioxide were observed in the exhalation air ten minutes after having taken the tablet. When the isotope-labelled urea was taken in aqueous solution, it was necessary to wait a further ten minutes before it could be said positively that the quantities of isotope-labelled carbon dioxide measured originated from urease in the stomach.

All of the aforesaid ten patients were treated with acid suppression medicine for a period of one week. Conventional urea-breath tests using isotope-labelled urea in aqueous solution showed a negative result in all cases.

When using isotope-labelled urea in solid preparation with an acid addition in accordance with the invention, the urease activity in the stomach of all ten patients was established.

TABLE 1

A compilation of the results obtained when diagnosing *Helicobacter pylori* with the aid of isotope-labelled urea in aqueous solution and in a solid preparation constructed in accordance with the invention.

| Method | Falsely positive 10 min. | Falsely positive 20 min. | Falsely negative 10 min. | Falsely negative 20 min. | Number of patients tested |
|---|---|---|---|---|---|
| Solution | 8 | 0 | — | — | 18 |
| Tablet | 0 | 0 | — | — | 18 |
| Solution + treatment with acid-secretion inhibitor | — | — | 10 | 10 | 10 |
| Tablet + treatment with acid-secretion inhibitor | — | — | 0 | 0 | 10 |

What is claimed is:

1. A pharmaceutical preparation for detecting the presence of urease activity only in the stomach in association with an infection by *Helicobacter pylori*, wherein said preparation consists of a solid, essentially water-free composition which comprises isotope-labelled urea in a form that is influenced by the activity of *Helicobacter pylori* in the stomach only, avoiding any non-Helicobacter (unspecific) urease activity in the oral cavity and the pharynx, and a solid, water-soluble acid to form a detectable reaction product, which accompanies exhaled air and is analyzed therein.

2. The preparation according to claim 1, wherein the isotope-labelled urea is labelled with $^{11}C$, $^{13}C$ and/or $^{14}C$.

3. The preparation according to claim 1, wherein the acid comprises at least one of the group of acids consisting of ascorbic acid, tartaric acid, citric acid and aciglumin.

4. The preparation according to claim 1, wherein the acid is present in an amount which will generate a pH of below 4 in the stomach.

5. The preparation according to claim 1, wherein said composition is formulated for a rapid dissolution in the stomach after having been administered.

6. The preparation according to claim 1, wherein the isotope-labelled urea has a particle size below 200 $\mu$m.

7. The preparation of claim 6, wherein the particle size is below 20 $\mu$m.

8. The preparation of claim 1, wherein the preparation is encapsulated and coated with soluble coating to prevent dissolution prior to reaching the stomach.

* * * * *